(12) United States Patent
Pond et al.

(10) Patent No.: US 6,302,692 B1
(45) Date of Patent: Oct. 16, 2001

(54) MULTI-VALVE DENTAL HANDPIECE SUPPLY RESERVOIR

(75) Inventors: Gary J. Pond, Racine, WI (US); Michael S. Butler, Round Lake Heights, IL (US)

(73) Assignee: Inter-Med, LLC., Racine, WI (US)

( * ) Notice: Subject to any disclaimer, the term of this patent is extended or adjusted under 35 U.S.C. 154(b) by 0 days.

(21) Appl. No.: 09/471,922

(22) Filed: Dec. 23, 1999

(51) Int. Cl.[7] .................................................. A61C 1/02
(52) U.S. Cl. .............................. 433/98; 433/100; 433/126
(58) Field of Search .............................. 433/80, 98, 100, 433/104, 126

(56) References Cited

U.S. PATENT DOCUMENTS

| | | | |
|---|---|---|---|
| 4,752,444 | * 6/1988 | Bowen et al. ........................ | 422/28 |
| 5,057,283 | * 10/1991 | Guggenheim et al. .............. | 422/116 |
| 5,318,443 | * 6/1994 | Overmyer ............................ | 433/104 |
| 5,348,711 | * 9/1994 | Johnson et al. ...................... | 422/300 |
| 5,526,841 | * 6/1996 | Detsch et al. .......................... | 137/15 |

* cited by examiner

*Primary Examiner*—Nicholas D. Lucchesi
(74) *Attorney, Agent, or Firm*—Ryan Kromholz & Manion, S.C.

(57) ABSTRACT

A fluid supply system that may be used interchangeably to supply fluid for use in dental instrumentation including irrigation, application, aeration, and evacuation for treating a patient's mouth. The fluid supply system includes a dental handpiece that has at least one valve arranged within and operably disposed upon said handpiece, and is used to allow flow between the fluid supply system and the patient's mouth. The fluid supply system can also be used to decontaminate dental unit water lines when used with antimicrobial fluids such as sodium hypochlorite.

30 Claims, 5 Drawing Sheets

MULTI-VALVE DENTAL HANDPIECE SUPPLY RESERVOIR

BACKGROUND OF THE INVENTION

1. Field of the Invention

This invention relates to systems and methods and methods for systems for providing micro-irrigation, aeration, evacuation and decontamination fluid to a dental hand tool and associated supply lines.

2. Description of the Prior Art

A. Dental Office Equipment

As a patient sits in a dental chair in a dentist's office, the dentist or a hygienist ordinarily cleans the patient's teeth with a variety of picks and brushes. Next, the dentist or a hygienist uses a hand held tool to supply rinse water, a variety of other medicament fluids, air, and vacuum from supply lines to a patient's mouth. U.S. patent application Ser. No. 09/054,277, filed on Apr. 2, 1998, and commonly assigned to the assignee hereof, discloses such a dental handpiece, and more particularly a handpiece that may be used interchangeably as an irrigator, an aerator, an applicator or as an evacuator for treating a patient's mouth.

The air lines in such a handpiece are commonly shared at the air supply with other air operated hand tools used in a dental office at the dentist's or hygienist's disposal. Therefore, the air supply pressure in each dental office is unique to that office because some dentists may operate more or less air tools from the same air supply.

Because of the high costs of high-speed hand tools, these tools are frequently only partially disposable between each patient. The permanent fixtures in a dental office, including the hardware, rinse water supply lines, fluid including air supply lines, and vacuum lines can become conduits for bacterial and disease transmission.

Infection control is a major concern in modern dental offices, with acquired immunodeficiency syndrome (AIDS) bringing this issue to the forefront. The spread of other communicable diseases and bacteria is also an important concern, from transmission of diseases ranging from staphylococcus to the common cold.

Modern dental offices take several precautions to minimize disease and bacterial transmission. First, high-speed hand pieces can be cleaned and decontaminated between each patient. Drills are routinely sterilized between each patient by autoclave, although some dentists only autoclave the equipment once a day or once every several days. Next, the high-speed hand tools and supply lines are designed to avoid retracting contaminated patient materials back into the handpiece (commonly referred to as "suck back") and easily spreading contamination to new patients. Additionally, prophylaxis angles are designed for disposal after each use, or alternatively, the prophy angles should be sealed and autoclaved between each patient. Last, either disposable air-water syringe tips should be placed over the air-water syringe and disposed after each use, or alternatively, the air-water syringe tips should be cleaned and autoclaved between each patient.

B. Dental Unit Water System Contamination

Even with all of these precautions, the liquid, air, and vacuum supply lines to the hand held tool are commonly known to accumulate contaminants that may lead to contaminant introduction into the patient's mouth or the air surrounding the patient's mouth. Collectively, these supply lines are referred to as dental unit waterlines (DUWL) although these lines often carry fluids other than water. The most common cause for DUWL contamination is the production of microbial biofilm on the interior of the lines supplying a high-speed handpiece or the air and fluid lines.

The microbial biofilm problem is exacerbated because pressurized cooling spray is used in the operation of the high-speed handpiece. The pressurization produces aerosols in the field of contamination, increasing the likelihood of microorganism transport through the easily communicable aerosol mechanism. Not only can the aerosol transport mechanism effect later patients through introduction of contaminants from improperly maintained tools, but also can effect the dental personnel subjected to spray within close proximity to the patient's mouth.

Several recent studies have demonstrated that the majority of organisms inhabiting biofilms are nonpathogenic bacteria. However, several additional more dangerous organisms including bacteria from the genera Legionella, Pseudomonas, Mycobacterium, Streptococci and Candida can contaminate the DUWL in unsafe levels, in particular *S. mutals, S. salivrius, S. mitis, P. aeruginosa, C. albicans*, chloroform, chlorodibromomethane, bromodichloromethane, bromoform, and trihalomethane.

In order to reduce both patient and dental personnel exposure to these harmful contaminants, researchers have identified several antimicrobial rinses for breaking down the biofilm present in the DUWL. These rinses include for example: Listerine®, Dentosept®, Bio2000®, Sodium Fluoride (NaF), chlorhexidine gluconate, Scope®, hydrogen peroxide, and sodium hypochlorite. The rinses are typically used in two different methods. The first method is to flush the system on a regular basis with the rinse and to discard the rinse because the rinse would contain elevated levels of biofilm. The second method is to continuously supply the rinse to the water line during regular dental operation to supply continuous antibacterial application. These compounds are known in the art and used to irrigate, debride and disinfect the mouth of a patient during instrumentation.

These rinses differ in efficacy and if the rinse is used during regular dental operation, some rinses have been shown to break down enamel bond strengths of composites etched to enamel, as is the case with patients having dentures, fillings or caps. Additionally, some rinses have very poor taste if used during regular operation. To date, sodium hypochlorite is the preferred rinse based on efficacy in reducing microbial counts and taste; however, sodium hypochlorite is highly corrosive with respect to metal components common to the dental systems.

Although DUWL decontamination has undergone improvements to reflect a greater understanding of the decontamination procedures necessary, shortcomings still persist. One such shortcoming is the inability to alternately irrigate, aerate, evacuate and decontaminate fluid lines with a single fluid supply system.

SUMMARY OF THE INVENTION

To overcome the above-identified concerns, the present invention provides a very inexpensive apparatus and method for a fluid supply system that is capable of supplying fluids for alternate irrigation, application, aeration, and decontamination.

The various components may be made using conventional molding and extrusion techniques from inexpensive materials, both relatively rigid and also very flexible when needed or required, and also resistant to sodium hypochlorite when required.

The fluid supply system comprises at least one reservoir capable of containing at least one of irrigation fluid, medicinal fluid, and decontamination fluid, a reservoir head detachably coupled to the reservoir, a fluid draw line communicatively coupled with the reservoir, a fluid outlet communicatively coupled with the fluid draw line, an air inlet, an air supply line communicatively coupled with the air inlet, and communicatively coupled with the reservoir head to supply pressurized air to the reservoir, the pressurized air forcing fluid from the reservoir through the of the fluid draw line to the fluid outlet, an air outlet communicatively coupled with the air supply line, and an air pressure regulator coupled with the air supply line between the air inlet and the reservoir. The fluid supply system can further comprise a vacuum inlet, and a vacuum outlet communicatively coupled with the vacuum inlet. The fluid supply system can further include a toggle switch to selectively supply pressurized air to either the first reservoir or the second reservoir, the toggle switch coupled with the air supply line. A housing top and bottom are provided as a convenient portal for connections.

A dental handpiece is also selectively communicatively coupled to at least one of the fluid outlet and the air outlet, the dental handpiece comprising a hand held housing having an interior, an exterior, a distal end, a proximal end, a top half, and a bottom half, a valve aperture through the top half of the hand held housing, an inlet aperture through the proximal end of the hand held housing, an outlet aperture through the distal end of the hand held housing, a manifold, the manifold having two inlets and one outlet, the manifold outlet contained in the interior of the hand held housing and extending through the outlet aperture, a lumen communicatively extending through the interior of the hand held housing from the inlet aperture to the manifold inlet, and a disposable tip selectively coupled to the manifold outlet. A valve regulating fluid output is also provided, the valve extending from the interior of the hand held housing to the exterior of the hand held housing through the valve aperture, the valve coupled with the lumen.

A method for supplying fluid to a dental handpiece or a dental unit water line is also disclosed, the method comprising attaching a fluid containing reservoir to a reservoir head, attaching a fluid line to a fluid outlet and to the dental handpiece, supplying pressurized air to the reservoir, the pressurized air forcing the fluid from the reservoir through at least one of a fluid draw line and a fluid outlet line, to the fluid outlet and through the fluid line to the dental handpiece, actuating a valve to allow the fluid to pass through the dental handpiece. A toggle switch can also toggle to a reservoir containing anti-microbial fluid if one is not already in-line.

A method of decontaminating dental unit water lines is also disclosed, the method comprising introducing an antimicrobial fluid into a fluid containing reservoir, attaching the fluid containing reservoir to a reservoir head, attaching a fluid line to a fluid outlet and to a dental unit water line, supplying pressurized air to the fluid containing reservoir, the pressurized air forcing the fluid from the reservoir through at least one of a fluid draw line and a fluid outlet line, to the fluid outlet and through the fluid line to a dental unit waterline, allowing the antimicrobial fluid to remain in the dental unit water line for a period of time sufficient to allow the anti-microbial fluid to destroy microbes present in the dental unit water line, and then flushing the system and disposing the flushed fluid. A toggle switch can also toggle to a reservoir containing anti-microbial fluid if one is not already in-line.

DETAILED DESCRIPTION

Although the disclosure hereof is detailed and exact to enable those skilled in the art to practice the invention, the physical embodiments herein disclosed merely exemplify the invention which may be embodied in other specific structure. while the preferred embodiment has been described, the details may be changed without departing from the invention, which is defined by the claims.

It is to be noted that like elements of the drawings are designated by like reference numbering.

The term fluid, as used herein, shall be defined as a gas, a liquid, a substance which flows, or a substance which differs from a solid in that it can offer no permanent resistance to change of shape. It shall further include mixtures of gases, mixtures of liquids, and mixtures of gases and liquids. The term fluid can include air, but the term air does not include fluids.

Figure 1:
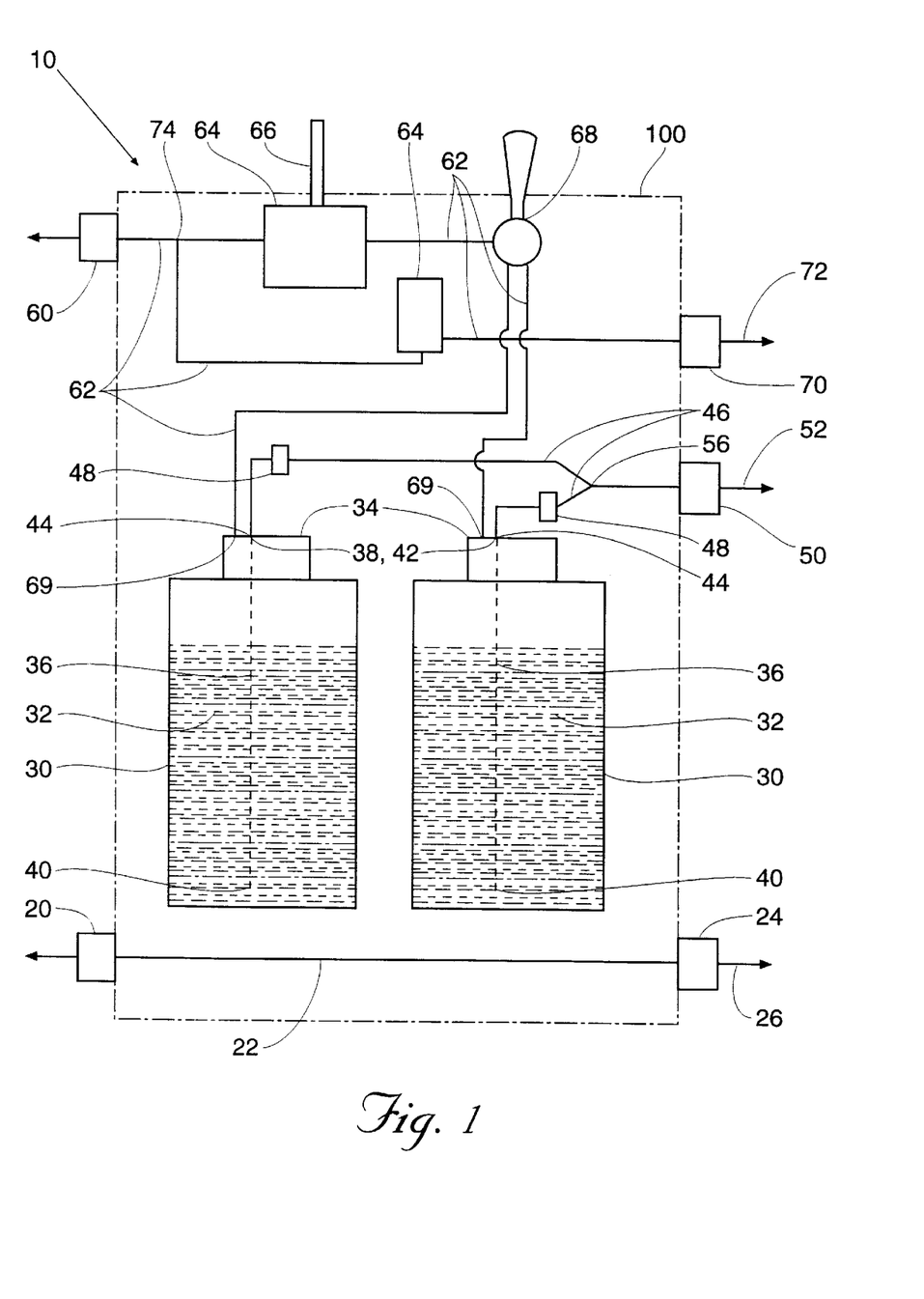
FIG. 1 is a schematic view of portions of a fluid supply system.
Figure 2:
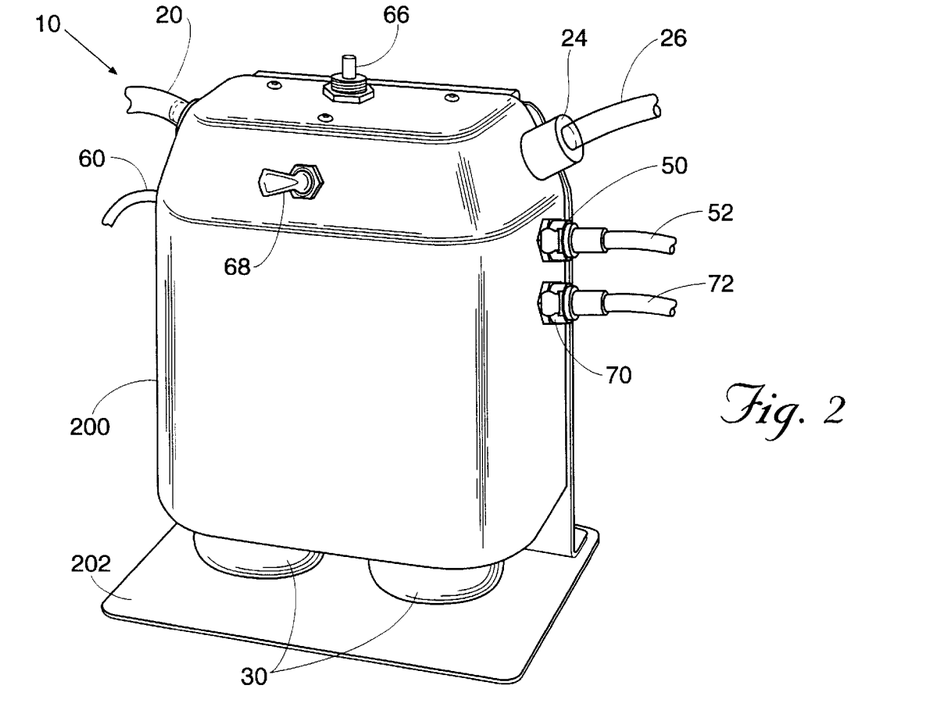
FIG. 2 is a perspective view of a fluid supply system.
Figure 3:
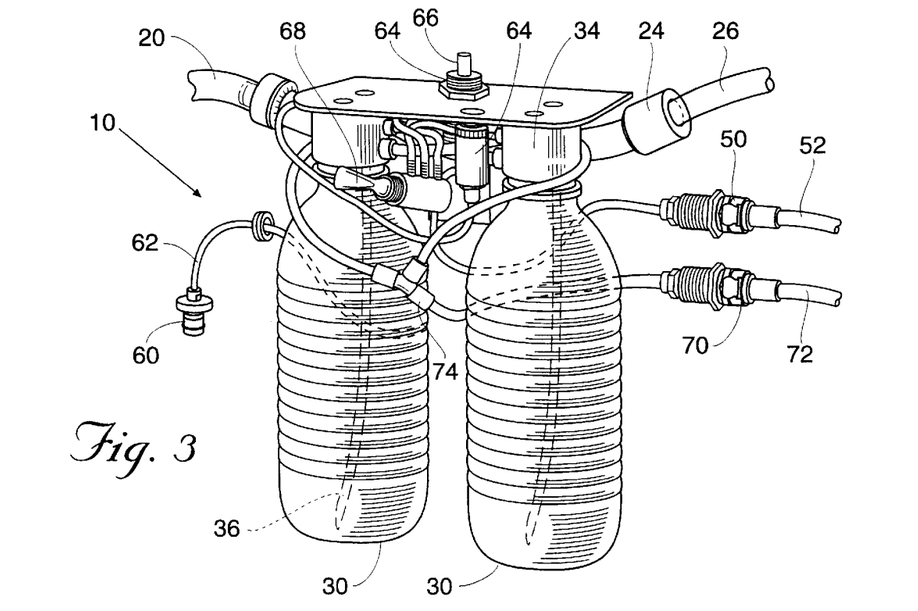
FIG. 3 is a perspective view of a fluid supply system, with a top and bottom housing cut away.

Referring to FIGS. 1, 2 and 3, a fluid supply system 10 capable of supplying irrigation, decontamination and aeration to a dental handpiece 80 or a dental unit waterline 54 is disclosed. The fluid supply system 10 includes a reservoir 30 capable of containing at least fluid 32 of irrigation fluid, medicinal fluid, and decontamination fluid. The reservoir 30 can come in many forms, including for example a bottle, a canister, a dual-compartment bottle or canister; and can range greatly in size. Preferably, however, the reservoir 30 is an inexpensive clear plastic bottle with a threaded opening, similar to a common water bottle with the cap removed.

Reservoirs of this type are readily available from a variety of sources and manufacturers, and are most commonly available in a 10–20 fluid ounce capacity size. The clear bottle allows for a determination of the amount of fluid 32 remaining in the reservoir 30, and a reservoir of this type is capable of withstanding internal pressure, though typically the resilience to pressure for this type of reservoir is limited to approximately 50 pounds per square inch (psi). Although a stronger reservoir is capable of use with the fluid supply system, such as a high density polyethylene reservoir, the polyethylene terephthalate elastomer (PETE) construction common to plastic soda and water bottles provides sufficient rigidity, is easily available, and is inexpensive.

The reservoir 30 is detachably coupled to a reservoir head 34. The reservoir head 34 is designed to provide the reservoir 30 with an air-tight seal capable of containing pressures up to 50 psi, but higher pressures are capable with different reservoir embodiments. Preferably, the detachable coupling is a threaded coupling, with a male thread on the reservoir 30, and the female thread on the reservoir head 34. The detachable coupling allows for quick and simple reservoir changes, should different fluids be desired for use with the fluid supply system 10.

Referring to FIGS. 1 and 3, the reservoir head 34 has an interior surface 33 and an exterior surface 35. The interior surface 33 contains two communicative conduits between the reservoir 30 and the remainder of the fluid supply system 10. The first communicative conduit provides a pathway to the interior of the reservoir for pressurized air or the air inlet fitting 69, and the second communicative conduit is a fluid inlet fitting 42, providing a pathway for fluid to leave the reservoir.

A fluid draw line 36 is coupled to the fluid inlet fitting 42 on the reservoir head. The fluid draw line 36 is sized to extend from the top of the reservoir 30 to the bottom of the reservoir 30 so that the fluid supply system 10 can operate until the reservoir 30 is nearly empty of fluid 32. A fluid outlet fitting 44 is communicatively coupled with the fluid inlet fitting 42, extending the pathway for fluid 32 leaving the reservoir 30, and coupled to the fluid outlet fitting 44 is a fluid outlet line 46. Preferably, the fluid outlet line 46 includes a check valve 48 coupled with the fluid outlet line 46, in order to prevent fluid 32 from flowing back into the reservoir 30. The fluid outlet line 46 terminates at a fluid outlet 50, used to connect the fluid supply system 10 with components of a dental handpiece 80 or with a dental unit water line 54.

Alternatively, the fluid draw line 36 and the fluid outlet line 46 could be integrated into one line serving the same purpose of providing a conduit for fluid 32 to leave the reservoir 30 and retain pressure within the reservoir 30, if an air-tight fitting around the line is used as opposed to a fluid inlet fitting 42 and fluid outlet fitting 44. However, the use of both the fluid draw line 36 and the fluid outlet line 46 along with the fluid inlet fitting 42 and the fluid outlet fitting 44 is preferred, mainly because this arrangement provides a better pressure seal than a single line with an air-tight fitting around the line.

Air is supplied to the reservoir by an air inlet 60, and an air supply line 62 communicatively coupled with the air inlet 60. The air supply line 62 is communicatively coupled with the reservoir head 34 and leads to the aforementioned first communicative conduit to supply pressurized air to the reservoir 30. The pressurized air is supplied to force fluid 32 from the reservoir 30 through a distal end 40 of the fluid draw line 36 through the fluid inlet fitting 42 and fluid outlet fitting 44 and through the fluid outlet line 46, and ultimately to the fluid outlet 50, components of the dental handpiece 80 or the dental unit water line 54.

The air supply line 62 is preferably split to provide two distinct pathways for air travel. The first pathway for air travel leads to the reservoir 30 as previously mentioned. The second pathway for air travel leads to an air outlet 70. Preferably, a common tee fitting 74 may be used to split the air flow, although two separate air supply lines could be used with one air line directed to the reservoir 30 and the other supply line directed to the air outlet 70. However, the tee fitting 74 used to split the one air supply line 62 into two pathways is preferred to minimize the number of fittings within the fluid supply system 10, and to simplify construction of the fluid supply system 10.

Preferably, both the fluid outlet 50 and the air outlet 70 are spring loaded female fittings, suitable for further connection to the dental handpiece 80 or the dental unit waterline 54.

The fluid supply system 10 also provides a central valve port for a vacuum line 26, another common necessity in dental instrumentation. A vacuum inlet 20, and a vacuum outlet 24 communicatively coupled with the vacuum inlet 20 are provided to simplify connections during instrumentation. The communicative coupling, or vacuum conveyor line 22 between the vacuum inlet 20 and the vacuum outlet 24 is constructed of a semi-rigid material capable of withstanding vacuum without collapsing.

Because of the desirability of the fluid supply system 10 to supply sodium hypochlorite at times, used to either irrigate, debride and disinfect the mouth of a patient, or to destroy bacteria present in the dental unit water line, the components of the fluid supply system 10 that come into contact with the sodium hypochlorite are preferably constructed of material capable of withstanding the corrosive effects of the sodium hypochlorite. These components, including the check valve 48, fluid draw line 36, fluid outlet line 46, fluid inlet fitting 42, fluid outlet fitting 44, fluid outlet 50, reservoir 30, reservoir head 34, and dental handpiece 80, are preferably constructed of sodium hypochlorite resistant material. Because sodium hypochlorite is particularly corrosive with respect to metal, non-metal components are preferred. Plastic is a preferred construction material because of its resistance to sodium hypochlorite corrosion.

Dental offices are often unique with respect to the air pressure in the air system. Dental offices operate at higher or lower pressures based on operator preference, the sizing of the air compressor, the number of components in the office using air, and the number of components in use at any one time. For this reason, the fluid supply system 10 is supplied with an air pressure regulator 64 coupled with the air supply line 62 between the air inlet 60 and the reservoir 30. This avoids erratic and uncontrollable fluid flow from the fluid supply system 10. Preferably, the air pressure regulator 64 is adjustable by operation of an air pressure regulator adjuster 66, giving an operator of the fluid supply system 10 the capability to alter the air pressure to provide a consistent output. One air pressure regulator that performs suitably is an AIRTROL R-920-03/35-3T 1–150 psi air pressure regulator.

In order to supply consistent air flow to the air outlet 70, the fluid supply system 10 contains a second air pressure regulator 64, the second air pressure regulator 64 coupled with the air supply line 62 between the air inlet 60 and the air outlet 70. The second air pressure regulator 64 could be adjustable, but preferably the second air pressure regulator 64 is set at an air pressure common to other dental aeration systems. A setting of approximately 20–40 psi is preferred by most dentists, with a setting of approximately 28 psi common.

In one embodiment of the present invention, the fluid supply system 10 is equipped with two reservoirs 30, a first reservoir 30 and a second reservoir 30, allowing the fluid supply system 10 to supply two different fluids 32 or twice the volume of the same fluid 32, with only one dental handpiece 80. The second reservoir 30 preferably operates and is connected to the fluid supply system 10 identically to the first reservoir 30.

The fluid outlet line 46 from the second reservoir 30 is coupled to at least one of the fluid outlet 50 and the first fluid outlet line 46. Preferably, the fluid outlet line 46 from the second reservoir 30 is coupled directly to the first fluid outlet line 46 with a Y-fitting 56, such that only one fluid outlet line 46 leads to the fluid outlet 50. Again, two fluid outlet lines 46 could lead to one or two fluid outlets 50, but a Y-fitting 56 allows for simplicity in tubing and construction.

In order for the operator to switch fluid supply from either divided portions of the first reservoir 30, or from the first to the second reservoir 30, a toggle switch 68 is provided to selectively supply pressurized air to the reservoir 30 from which fluid is desired. Alternatively, a foot pedal could be used to toggle between reservoirs 30. However, the toggle switch 68 is the preferred toggle mechanism because of simplicity.

The pressurized air is supplied to force fluid 32 from the reservoir 30 through the distal end of the fluid draw line 40 through the fluid inlet fitting 42 and fluid outlet fitting 44 and through the fluid outlet line 46, and ultimately to the fluid outlet 50, components of the dental handpiece 80 or the dental unit water line 54.

Preferably, the toggle switch 68 maintains air pressure within the reservoir 30 not receiving the supply of pressurized air. This allows the operator to quickly supply the desired fluid following a toggle of the toggle switch 68, as opposed to having to wait for the air supply to re-pressurize the reservoir 30 with each alternation in fluid.

Referring to FIG. 2, the fluid supply system 10 is supplied with a housing top 200 and a housing bottom 202, provided as a hub for simple instrumentation configuration changes, and as a hub for the fluid supply system 10 components. Preferably, a space between the housing top 200 and the housing bottom 202 allows for viewing the reservoir 30 to determine the amount and the type of fluid 32 contained in the reservoir 30. The housing top 200 and the housing bottom 202 should be readily detachable from each other, either by screw means or snap means, because the reservoirs 30 will require intermittent change to change between different types of fluids 32. The housing top 200 and housing bottom 202 create an attractive portal for quick connections and flexibility during instrumentation, and also provide an easily accessible outside surface for toggling the toggle switch 68 and regulating the air pressure with the air pressure regulator switch 66.

During instrumentation, an operator can configure the fluid supply system 10 to supply different fluids 32 and finger tip controlled irrigation, aeration and evacuation to a patient's mouth. The operator can connect the fluid outlet 50 by a fluid line 52 and the air outlet 70 by an air line 72 and the vacuum outlet 24 by a vacuum line 26 to the dental handpiece 80, or any combination of the outlets to the dental handpiece 80.

Figure 4:
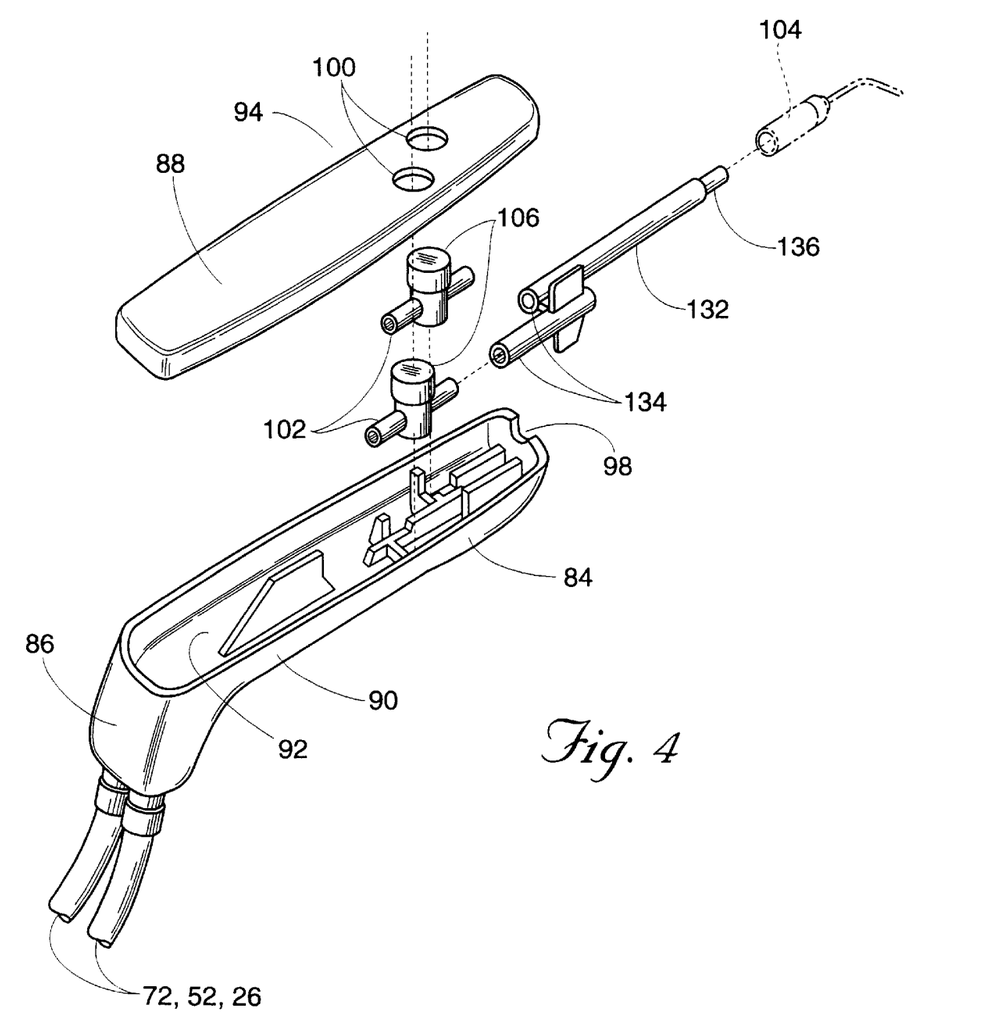
FIG. 4 is a perspective view of a dental handpiece of the fluid supply system, with the components shown in an exploded view.
Figures 5, 6:
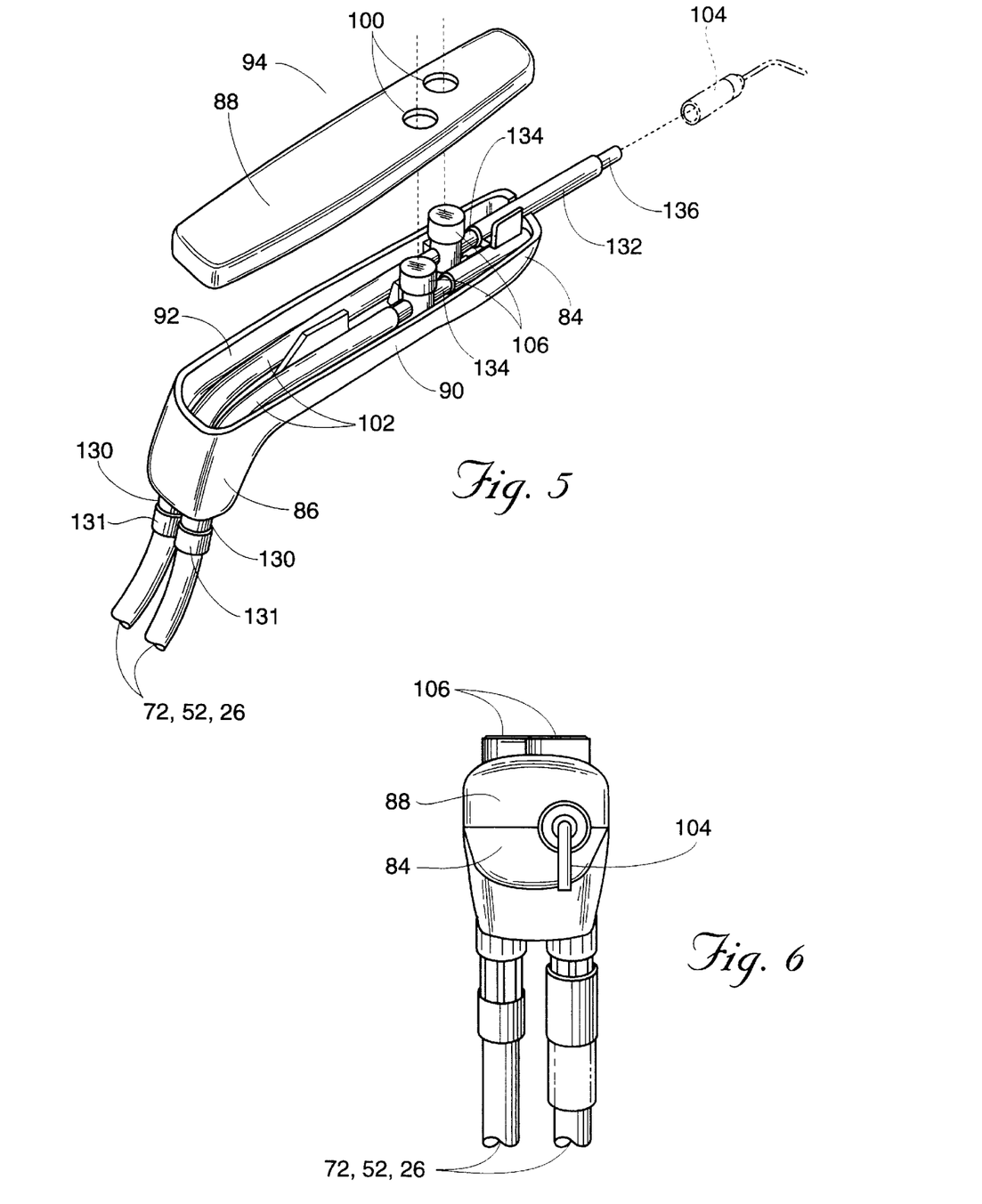
FIG. 5 is a perspective view of the dental handpiece, with the components excepting a top half of the hand held housing assembled.
FIG. 6 is a perspective view of the dental handpiece from the perspective of a patient's mouth.

Referring now to FIGS. 4–6, the dental handpiece 80 is a hand held housing 82 having an interior 92, an exterior 94, a distal end 84, a proximal end 86, a top half 88, and a bottom half 90. An inlet aperture 96 is provided through the proximal end 86 of the hand held housing 82, and the inlet aperture 96 may be fitted to a conventional male luer lock member 130 for easy connection between the dental handpiece 80 and the fluid supply system 10 including the fluid outlet 50 by the fluid line 52 and the air outlet 70 by the air line 72 and the vacuum outlet 24 by the vacuum line 26. Preferably, the air line 72, fluid line 52, and vacuum line 26 are disposable flexible supply lines, with the vacuum line rigid enough to avoid collapse under vacuum conditions, and the lines fitted with a conventional female luer lock member for 131 connection with the male luer lock member 130. Preferably, two male luer lock members 130 are supplied with the dental handpiece 80 such that two lumens 102 may be coupled with the male luer lock members 130 in the interior 92 of the hand held housing 82.

Preferably, the hand held housing 82 is of two-piece construction, with a top half 88 one piece, and a bottom half 90 the second piece. The two-piece construction allows for ease in assembling and disassembling the dental handpiece 80 for autoclaving.

A valve aperture 100 through the top half 88 of the hand held housing 82 allows finger operation of a valve 106 regulating fluid output, the valve 106 extending from the interior 92 of the hand held housing 82 to the exterior 94 of the hand held housing 82 through the valve aperture 100. The valve 106 is preferably a trumpet valve chosen for low cost and simplicity in operation. The valve 106 is directly engageable with two lumens 102 one for each inlet fitted within and longitudinally extending through the interior 92 of the handpiece 82.

The valve 106 of the handpiece is not entirely unlike a conventional "trumpet valve", such as that disclosed in the application Ser. No. 09/174,751 entitled "Multi-Valve Dental Handpiece".

Downstream of the valve 106 along the lumen 102 in the interior 92 of the hand held housing 82, the lumen 102 is coupled with a manifold 132, the manifold 132 having two inlets 134 for connection with lumens 102, and one outlet 136, the manifold outlet 136 extending through an outlet aperture 98 through the distal end 84 of the hand held housing 82. The manifold outlet 136 extends longitudinally from the valve 106 and is arranged to receive a conventional disposable applicator/evacuation tip 104 or cannula or irrigation dental tip or cannula. The disposable tip 104 is selectively coupled to the manifold outlet 136, and the disposable tip 104 is then used during instrumentation to direct the deposit of fluids or evacuation target site in a patient's mouth.

To supply fluid 32 to the dental handpiece 80, an operator first attaches one or more fluid containing reservoirs 30 to the reservoir head 34 or heads 34. Next, the operator attaches a fluid line 52 to the fluid outlet 50 and to the dental handpiece 80 by way of coupling the luer lock male member 130 with the luer lock female member 131. If the fluid supply system 10 is supplied with a toggle switch 68, as is preferable, the operator toggles the toggle switch 68 to select which reservoir 30 to force fluid 32 from, the toggle switch 68 directing the pressurized air to either the first or the second fluid containing reservoir 32. Next, the operator supplies pressurized air to the reservoir 30, the pressurized air forcing the fluid 32 from the reservoir 30 through at least one of the fluid draw line 36, the fluid inlet fitting 42, and fluid outlet fitting 44, and through the fluid outlet line 46, and ultimately to the fluid outlet 50 and through the fluid line 52 to the dental handpiece 80.

Figure 7:
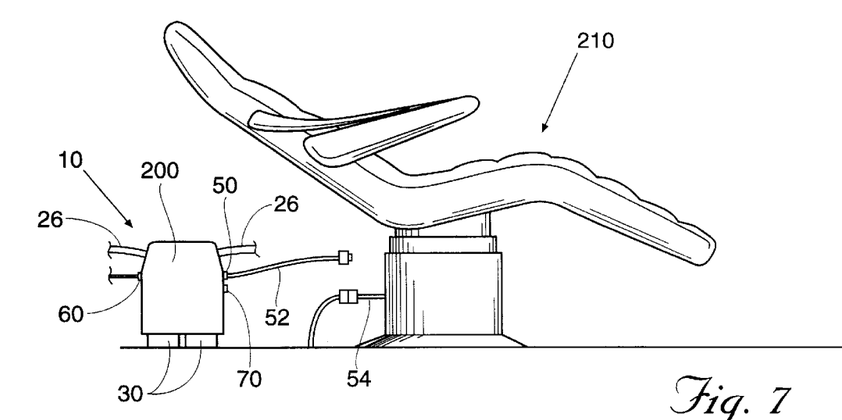
FIG. 7 is a front elevational view of a dental unit water line hooked up to a water supply line.
Figure 8:
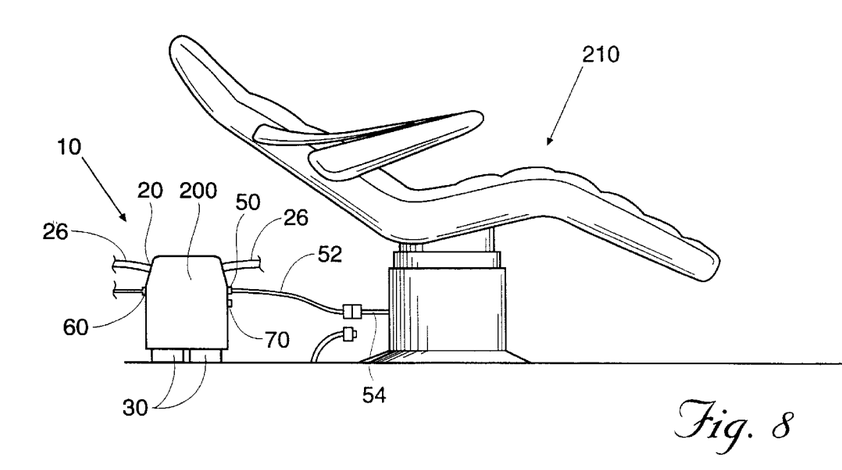
FIG. 8 is a front elevational view of the fluid supply system connected to a dental unit water line for decontamination, and the water supply line disconnected.

Referring now to FIGS. 7 and 8, to decontaminate dental unit water lines, the fluid supply system 10 and the fluid line 52 may be directly coupled with the dental unit water line 54 on the dental chair 210, as opposed to coupled with the dental handpiece 80.

Referring to FIGS. 1 and 8, during decontamination, the operator introduces an anti-microbial fluid such as sodium hypochlorite into the reservoir 30, and attaches the reservoir 30 to the reservoir head 34. Next, the operator attaches the fluid line 52 to the fluid outlet 50 and to the dental unit water line 54, and if the fluid supply system 10 is supplied with a toggle switch 68, as is preferable, the operator toggles the toggle switch 68 to select which reservoir 30 to force fluid 32 from, the switch 68 directing the pressurized air to the reservoir 30 containing the anti-microbial fluid 32. Next, the operator supplies pressurized air to the antimicrobial fluid containing reservoir 30, the pressurized air forcing the antimicrobial fluid from the reservoir 30 through at least one of the fluid draw line 36, the fluid inlet fitting 42, and fluid outlet fitting 44, and through the fluid outlet line 46, and ultimately to the fluid outlet 50 to the dental unit waterline 54. The antimicrobial fluid 32 is allowed to remain in the dental unit water line 54 for a period of time sufficient to allow the anti-microbial fluid to destroy microbes present in the dental unit water line 54, and an overnight period is recommended to allow a lengthy exposure time.

Following an exposure period sufficient to destroy the microbes, the operator can flush the dental unit water line 54 by either toggling the toggle switch 68 to select a different reservoir 30, or flushing with anti-microbial fluid 32, or purging with air from the air line 72. The operator next supplies pressurized air to the chosen reservoir 30, the pressurized air forcing the fluid 32 from the reservoir 30 through at least one of the fluid draw line 36, the fluid inlet fitting 42, and fluid outlet fitting 44, and through the fluid outlet line 46, and ultimately to the fluid outlet 50 to the dental unit waterline 54. Because the flushed fluid will contain elevated levels of contaminants, it is preferable to discard the flushed fluid from the dental unit waterline 54.

Accordingly, the invention comprises a fluid supply system 10 whereby the dentist can supply fluids 32 that irrigate the field of operation within a patient's mouth with water, apply medicine to the field of operation, evacuate excess fluid 32 or debris from the field of operation, and supply fluid 32 to decontaminate dental unit water lines 54. The irrigation, application, and evacuation functions are controlled by the valves 106 on the dental handpiece that is connected with air supply line 72, fluid supply line 52 or vacuum line 26.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A fluid dispensing assembly comprising:
    a fluid supply system;
    a dental handpiece, said dental handpiece located externally of said fluid supply system;
    a plurality of fluid outlet lines disposed on said fluid supply system;
    a plurality of fluid inlets disposed on the dental handpiece;
    said fluid outlet lines being removably coupled to said fluid inlets;
    the system having a first reservoir and a second reservoir; said second reservoir capable of containing at least one of irrigation fluid, medicinal fluid, or decontamination fluid;
    a first reservoir head detachably coupled to the first reservoir;
    a second reservoir head detachably coupled to the second reservoir;
    a first fluid draw line contained within the first reservoir, the first fluid draw line detachably coupled with a fluid outlet line;
    a second fluid draw line communicatively coupled with the second reservoir, the second fluid draw line having a proximal end and a distal end;
    a first fluid outlet line communicatively coupled between the fluid and the dental handpiece;
    a second fluid outlet line communicatively coupled with the proximal end of the second fluid draw line;
    an air supply line communicatively coupled with the first reservoir head to supply pressurized air to the reservoir from a first air inlet, the air pressurized at a pressure capable of forcing fluid from the reservoir through the fluid outlet line;
    a second air inlet;
    the air supply line communicatively coupled with the second air inlet, and communicatively coupled with the second reservoir head to supply pressurized air to the second reservoir, the pressurized air forcing fluid from the second reservoir through the distal end of the second fluid draw line to the second fluid outlet.

2. A fluid supply system according to claim 1, the system further comprising:
    a second fluid outlet line having a proximal end and a distal end;
    a second fluid inlet fitting and a second fluid outlet fitting coupled to the second reservoir head;
    the proximal end of the second fluid draw line coupled with the second fluid inlet fitting, the distal end of the second fluid outlet line coupled to the second fluid outlet fitting, the proximal end of the second fluid outlet line coupled to at least one of the fluid outlet and the first fluid outlet line.

3. A fluid supply system according to claim 1, the system further comprising:
    a toggle switch to selectively supply pressurized air to either the first reservoir or the second reservoir, the toggle switch coupled with the air supply line.

4. A fluid supply system according to claim 3, wherein the toggle switch maintains pressure the reservoir not receiving the supply of pressurized air.

5. A fluid supply system according to claim 4, the system further comprising:
    a housing bottom;
    the housing bottom detachably coupled to the housing top.

6. A fluid supply system according to claim 1, the system further comprising:
    a housing top;
    the housing top coupled to the reservoir head.

7. A fluid supply system according to claim 1, the system further comprising:
    a housing top;
    the housing top coupled to the first reservoir head and the second reservoir head.

8. A fluid supply system according to claim 1, the system further comprising:
    the dental handpiece selectively communicatively coupled to at least one of the fluid outlet and the air outlet and the vacuum outlet.

9. A fluid dispensing assembly comprising:
    a fluid supply system;
    a dental handpiece;
    a plurality of fluid outlet lines disposed on said fluid supply system;
    a plurality of fluid inlets disposed on the dental handpiece;
    said fluid outlet lines being removably coupled to said fluid inlets;
    the fluid supply system further including:
        a reservoir; a volume of fluid contained within the reservoir; a reservoir head detachably coupled to the reservoir; a fluid outlet line communicatively coupled between the fluid and the dental handpiece;

an air supply line communicatively coupled with the reservoir head to supply pressurized air to the reservoir, the air pressurized at a pressure capable of forcing fluid from the reservoir through the fluid outlet line; a fluid draw line contained within the reservoir, the fluid draw line detachably coupled with the fluid outlet line; the dental handpiece selectively communicatively coupled to at least one of the fluid outlet and the air outlet and the vacuum outlet; and wherein the dental handpiece further includes:
- a hand held housing having an interior, an exterior, a distal end, a proximal end, a top half, and a bottom half;
- a valve aperture through the top half of the hand held housing;
- an inlet aperture through the proximal end of the hand held housing;
- an outlet aperture through the distal end of the hand held housing;
- a manifold, the manifold having two inlets and one outlet, the manifold outlet contained in the interior of the hand held housing and extending through the outlet aperture;
- a lumen communicatively extending through the interior of the hand held housing from the inlet aperture to the manifold inlet;
- a disposable tip selectively coupled to the manifold outlet;
- a valve regulating fluid output, the valve extending from the interior of the hand held housing to the exterior of the hand held housing through the valve aperture, the valve coupled with the lumen.

10. A fluid supply system according to claim 1, wherein the reservoir contains at least one of sodium hypochlorite, water, and medicinal fluid.

11. A fluid dispensing assembly comprising;
a fluid supply system;
a dental handpiece;
a plurality of fluid outlet lines disposed on said fluid supply system;
a plurality of fluid inlets disposed on the dental handpiece;
said fluid outlet lines being removably coupled to said fluid inlets;
the fluid supply system further including:
- a reservoir;
- a volume of fluid contained within the reservoir;
- a reservoir head detachably coupled to the reservoir;
- a fluid outlet line communicatively coupled between the fluid and the dental handpiece;
- an air supply line communicatively coupled with the reservoir head to supply pressurized air to the reservoir, the air pressurized at a pressure capable of forcing fluid from the reservoir through the fluid outlet line;
- a fluid draw line contained within the reservoir, the fluid draw line detachably coupled with the fluid outlet line;
- the dental handpiece selectively communicatively coupled to at least one of the fluid outlet and the air outlet and the vacuum outlet; and
wherein the dental handpiece further includes:
- a hand held housing having an interior, an exterior, a distal end, a proximal end, a top surface, and a bottom surface;
- a valve aperture through the top surface of the hand held housing;
- an inlet aperture through the proximal end of the hand held housing;
- an outlet aperture through the distal end of the hand held housing;
- a manifold, the manifold having two inlets and one outlet, the manifold outlet contained in the interior of the hand held housing and extending through the outlet aperture;
- a lumen communicatively extending through the interior of the hand held housing from the inlet aperture to the manifold inlet;
- a disposable tip selectively coupled to the manifold outlet;
- a valve regulating fluid or vacuum output, the valve extending from the interior of the hand held housing to the exterior of the hand held housing through the valve aperture, the valve coupled with the lumen.

12. A method of supplying fluid to a dental hand piece comprising the steps of providing the fluid supply system of claim 3, and utilizing the fluid supply system to supply fluid to a dental handpiece.

13. A fluid supply system according to claim 9, the fluid outlet line having a proximal end and a distal end, the system further comprising:
a fluid inlet fitting and a fluid outlet fitting coupled to the reservoir head;
the proximal end of the fluid draw line coupled with the fluid inlet fitting, the distal end of the fluid outlet line coupled to the fluid outlet fitting, the proximal end of the fluid outlet line coupled to the fluid outlet.

14. A fluid supply system according to claim 13, the system further comprising:
a check valve coupled with the fluid outlet line.

15. A fluid supply system according to claim 14, wherein the check valve, fluid draw line, fluid outlet line, fluid outlet, reservoir, and reservoir head are constructed of sodium hypochlorite resistant material.

16. A fluid supply system according to claim 15, wherein the sodium hypochlorite resistant material is plastic.

17. A fluid supply system according to claim 9, the system further comprising:
an air pressure regulator coupled with the air supply line between the air inlet and the reservoir.

18. A fluid supply system according to claim 17, wherein the air pressure regulator is adjustable.

19. A fluid supply system according to claim 9, the system further comprising:
a second air pressure regulator, the second air pressure regulator coupled with the air supply line between the air inlet and the air outlet.

20. A fluid supply system according to claim 9, wherein the fluid outlet is a spring loaded female fitting.

21. A fluid supply system according to claim 9, wherein the air outlet is a spring loaded female fitting.

22. A fluid supply system according to claim 1, said first and second fluid outlet lines each having a proximal end and a distal end, the system further comprising:
a first fluid inlet fitting and a first fluid outlet fitting coupled to said first reservoir head;
a second fluid inlet fitting and a second fluid outlet fitting coupled to said second reservoir head;
the proximal end of the second fluid draw line coupled with the second fluid inlet fitting, the distal end of the second fluid outlet line coupled to the second fluid outlet fitting, the proximal end of the second fluid outlet line coupled to the fluid outlet.

23. A fluid supply system according to claim 22, the system further comprising:
a first check valve coupled with the first fluid outlet line and a second check valve coupled with the second fluid outlet line.

24. A fluid supply system according to claim 23, wherein the check valve, fluid draw lines, fluid outlet lines, fluid outlet, reservoirs, and the reservoir heads are constructed of sodium hypochlorite resistant material.

25. A fluid supply system according to claim 24, wherein the sodium hypochlorite resistant material is plastic.

26. A fluid supply system according to claim 1, the system further comprising:
an air pressure regulator coupled with the air supply line between the air inlet and the first and second reservoirs.

27. A fluid supply system according to claim 26, wherein the air pressure regulator is adjustable.

28. A fluid supply system according to claim 1, the system further comprising:
a second air pressure regulator, the second air pressure regulator coupled with the air supply line between the air inlet and the air outlet.

29. A fluid supply system according to claim 1, wherein the fluid outlet is a spring loaded female fitting.

30. A fluid supply system according to claim 1, wherein the air outlet is a spring loaded female fitting.

* * * * *